United States Patent [19]

Keshavaraja et al.

[11] Patent Number: 5,932,752
[45] Date of Patent: Aug. 3, 1999

[54] PROCESS FOR THE C-C BOND FORMING REACTION USING SOLID ACID CATALYSTS

[75] Inventors: Alive Keshavaraja; Vishnumurthy Ramachandra Hegde; Pradeep Kumar; Sooryakant Ganesh Hegde; Arumugamangalam Venkataraman Ramaswamy; Thottappillil Ravindranathan, all of Maharashtra, India

[73] Assignee: Council of Scientific and Industrial Research, New Delhi, India

[21] Appl. No.: 08/654,665

[22] Filed: May 29, 1996

[30] Foreign Application Priority Data

Dec. 29, 1995 [IN] India ............................. 2476/DEL/95

[51] Int. Cl.$^6$ ................................................ C07D 303/38
[52] U.S. Cl. ............................................................ 549/549
[58] Field of Search ............................................. 549/549

*Primary Examiner*—Amelia Owens
*Attorney, Agent, or Firm*—Ladas & Parry

[57] ABSTRACT

A process for the preparation of organic compounds through C—C bond forming reaction which comprises reacting a diene with a dienophile in the presence of solid acid based on either yttrium, scandium or lanthanum supported on metal oxide supports such as oxides of zirconium or tin or titanium or iron oxide modified by sulphation as catalysts for a period ranging from 5 to 48 hours and recovering the reaction products from the reaction mixture by filtration and removal of the solvent by evaporation followed by column chromatography.

10 Claims, No Drawings

PROCESS FOR THE C-C BOND FORMING REACTION USING SOLID ACID CATALYSTS

The present invention relates to an improved process for the preparation of organic compounds through carbon-carbon (C—C) bend forming reactions. The present invention more particularly relates to a process for preparing organic compounds through C—C bond forming reactions such as Diels-Alders reactions, Hetero Diels-Alders reaction and ene reaction. Still more particularly, the present invention relates to a process for the preparation of organic compounds through C—C bond formation in the above reactions in presence of the solid acids as catalysts such as yttrium oxide doped in sulfated metal oxide where, metal oxides are selected from zirconia, tin oxide titania or iron oxide Also, other catalysts used in the present invention may contain scandia (scandium oxide) or lanthana (lanthanum oxide) supported on the above mentioned solid acids.

Diles-Alder reaction is one of the key steps and the most exciting frontiers in the synthesis of natural products. Thermal addition of an olefin to a conjugated diene gives a six membered ring and this reaction is popularly known as Diels-Alder (D-A) Reaction (hereinafter referred to as D-A reaction).

D-A reaction is Chemo-, regio-, stereo-, and enantio selective with appropriate substrates and up to 4 continuous chiral centers can be produced in one step. Many variants known in the prior art includes normal D-A, inverse electron demand D-A, hetero D-A, intramolecular D-A and asymmetric D-A. All these reaction offer opportunity of enormous proportions for synthetic organic chemist. Several ways of catalysing D-A reaction is known in the prior art. Some of the prominent approach involves application of high pressure, Lewis acid, Sonochemistry, photochemistry, microwave, solvent variation and lithium perchlorate in ether etc.

In the prior art, the D-A reactions were catalytically carried by homogeneous route by using inorganic Lewis acids such as aluminium chloride, stannic chloride or titanium chloride (Europian Patent Application, EP 325,000, Jul. 26, 1989; Ger Offen. DE, 3,235,399, Mar. 29, 1984, Ger.Offen., 2,361,138, Jun. 12, 1974). Attempts have also been made in the prior art to catalyse Diels-Alder reaction/cyclo-addition reactions and other allied reaction using several Lewis acids such as $ZnCl_2$— (complexed with ethers), $ZnBr_2$, $BF_3$ Eu (III) complexes, Yb (III), Sc(III) and Y(III) complexes. Also, it is known in the prior art that, the D-A reactions were carried out with yttrium compounds in a homogeneous media. The recent efforts by Evans to use $YI_3$— as a catalyst for chiral reduction in the presence of a suitable auxilliary and by Kobayashi to use $Y(OTf)_3$— as a Diels-Alder catalysts were unsuccessful. (Ref. Evans et.al., J. Am. Chem. Soc., 1993, 115, 9800 and Kobayashi et.al., Tetrahedron Lett. 1993, 34, 3755)

In the prior art, some of the dienophiles pose a great difficulty in reacting under varied D-A reaction conditions. For example, 7-isopropyl-10-methyl-oxaspiro(5.5)undec-3-ene-2,5-dione reacts under a variety of D-A conditions such as refluxing in high boiling solvents, neat heating, sealed tube heating or ultra sound accelaration with or with out various well known Lewis acids such as BF3, TiCl4— etc. to give D-A products in not more than 10% yield.

Also, there are several other limitations in using these as catalysts because of the major drawback of the methods known in the prior art such as, i) difficulty involved in recovery and the separation of the catalyst from the products, ii) high cost of the materials involved, iii) higher reaction temperature such as 100° C. or more, iv) difficulty in the work up procedure during the homogeneous catalytic route, v) difficulty in handling of catalyst material such as stannic chloride or aluminium chloride, vi) poor endo-selectivity, vii) lack of reusability of the catalyst.

In view of the above mentioned drawbacks of the prior art process, it is desirable to develop an improved process for accelarating the various C—C bond forming reactions.

The significant feature of the present invention are:

The C—C bond formation in Diels-Alder and ene reaction, according to the present invention, occurs realtively at lower temperature, preferably at room temperature.

The process makes use of non-hazardous solid catalysts, easy to recover and not being prone to explosions.

The process leads to high yields (above 75%) of the desired products.

The process is feasible in heterogeneous media.

It has been found according to the present invention, that the yttrium, scandium or lanthanum based strong Lewis acid solid catalyst can be sucessfuly employed for various C—C bond forming reactions such as D-A reaction, hetero D-A reaction and ene reaction. The yttrium, scandium or lanthanum based strong Lewis acid catalyst has been found to accelerate the D-A reaction between variety of dienes and dienophiles. The D-A products were obtained in moderate to excellent yields with high selectivity of endo product.

The major reason for the improved activity and selectivity is speculated to be due to the oxophilic nature of the group III B elements (i.e yttrium scandium and lanthanum), there by lowering the HOMO of diene and LUMO of dienophile.

It is a well known fact that Lewis acid catalysed cycloadditions not only proceed more rapidly but also are generally regio and stereoselective. Theoretical interpretations of the acceleration as well as the selectivity in these Lewis acid catalysed reactions have been proposed. The latest frontier molecular orbital theory (FMO) successfully explains the role of the Lewis acid catalysts. According to this theory, donor-acceptor interactions between the dienophile and the catalyst lowers the energy of the HOMO (highest occupied molecular orbital) and the LUMO (lowest unoccupied molecular orbital) of the dienophile. This means that the separation between the molecular orbitals will decrease and the stabilization of the transition state will increase explaining the rate acceleration under the above Lewis acid catalysts.

Accordingly, the present invention provides a process for the accelaration of the C—C bond forming reaction using the superacid catalyst prepared by the process described in the co-pending patent specification, 2477/DEL/95 U.S. application pending which comprises of reacting a diene with dienophile in presence of solid acid based on either yttrium or scandium or lanthanum supported on metal oxide supports such as oxides of zirconium or tin or titanium or iron oxide modified by sulphation as catalysts preferably at room temperature for 5 to 48 hours and recovering the reaction products from the reaction mixture by filtration and removal of the solvent followed by column chromatography.

According to the process of the present invention, the catalyst(s) used is (are) highly acidic material. The catalyst composite used in the process of the present invention are sulfated metal oxides modified with group III B transition metal oxides, prepared according to a procedure described in the process of the co-pending patent application No. 2477/DEL/95 U.S. application pending.

The main constituent of the catalyst used may be either zirconia or tin oxide or titanium oxide or iron oxide all doped with sulphates and modified with either yttria or lanthana or scandia.

According to an embodiment of the process of the present invention, a variety of substrates, i.e., diene and denophiles are employed for D-A reaction.

A number of dienes such as cyclopentadiene, 1,3-cyclohexadiene, methyl-1,3-butadiene, 2-trimethylsilyloxy-1,3-butadiene, 1-methoxy-3-trimethylsilyloxy-1,3-butadiene, acrolein, furan, benzoisofuran, 1-methoxy-1,3-cyclohexadiene, hexachlorocyclopentadiene, 2,3-dimethylbutadiene, 1-methoxy-1,3-butadiene and 4-methoxyisoxazoles are used for the reaction.

Dienophiles such as 1,4-napthoquinone, 2-methyl-1,4-napthoquinone, benzoquinone, cyclohexanone, acrylic acid, ethyl or methyl acrylate, 3,4-dihydro-2H-pyran-spiro(4.4) non-2,3-ene-1,4-dione, 7-isopropyl-10-methyl-1-oxaspiro (5.5)undec-3-ene-2,5-dione, 10-phenyl-1-oxaspiro(5,5) cyclohexyl-3-ene-2,4-dione, N-ethylmaleimide, 2,5-dihydrothiophene-3,4-dicarboxylic anhydride, Dialkyl, diaryl or aryl-alkyl maleates and fumarates, imines, alkyl or aryl glyoxalates, alkyl or aryl pyruvates, vinyl ethers, cis-butenediol derivatives and cyclic sulfites and ketals are used for the reaction.

According to another feature of the present invention, in order to make the reaction to proceed smoothly and to obtain good results, the amount of diene as substrate is preferably fixed to be 1.2 to 10 times (by mole) that of dienophile and the catalyst amount ranging from 10% to 50% (by weight) with respect to dienophile. In most cases, 20 mole % excess of the diene is sufficient for the efficient D-A which is usually not the case when conventional homogeneous catalysts were used in the prior art.

According to another feature of the present invention, the reaction is carried out in the presenec of solvent(s) like dichloromethane, chloroform, carbon tetrachloride and tetrahydrofuran whcih leads to a faster reaction due to homogenization of the reaction mixture. The solvent used may be either any one of the above or mixtures thereof A yet another important feature of the process of the present invention is that Group IIIB transition metal containing catalyst composites is employed in heterogeneous medium for the first time. Until now, Yttrium, Scandium and Lanthanum were used as part of the homogeneous catalytic complexes for C—C coupling reactions. The solid catalysts thus used can be recovered and reused. The mixture of diene, dienophile and the catalyst in dichloromethane may be mixed preferably at room temperature for time ranting from 5 to 48 hours, the progress of the reaction is monitored by thin layer chromatography (TLC), filtering off the catalyst, removing the solvent by rotary evaporator followed by chromatoraphing the residue over silica gel column by eluting with 5% acetone/petroleum ether to give high selectivity of endo-adduct.

The process of the present invention is further illustrated by the following examples, which may not however be construed to limit the scope of the present invention.

EXAMPLE 1

In this example, the preparation of yttrium based solid acid catalysts is discussed. A mixture of yttrium nitrate and zirconyl nitrate in the molar ratio of 16:84 was added to 28% aqueous ammonia under constant stirring until a pH of 8.5 so as to get a precipitate. The precipitate was washed with deionised water, dried at 110° C. for 12 hours and treated with 2 M ammonium sulphate solution,, dried again at 120° C. for 24 hour and subsequently calcined at 500° C. for 8 hour. A highly acidic material was thus obtained, whose chemical composition (as determined by XRF technique) was found to be 82.6 mole % of Zr, 15.6 mole % of Y and 1.8 mole % of S. The physico-chemical characterization of the catalyst was carried out by XRD, FTIR, potentiometric titration, temperature programmed desorption (TPD), SEM and $N_2$— adsorption technique. The X-ray powder diffraction profile of the catalyst showed the formation of cubic phase. IR spectra of the pyridine adsorbed on the solid catalyst showed absorption bands at 1640, 1605, 1577, 1542, 1490 and 1444 $cm^{-1}$. The strong absorption band at 1444 $cm^{-1}$ indicated the presence of co-ordinated pyridine on the Lewis acid sites of the catalysts. The presence of the few Bronsted acid sites are indicated by the absorption band at around 1542 $cm^{-1}$ of the pyridinium ion. The potentiometric titrations of the acid sites with n-butyl amine in nonaqueous medium showed the influence of yttria in enhancing the number of acid sites. The presence of very strong acid sites in the catalyst is indicated by the peak maxima at 530° C. in the TPD profile. The scanning electron micrographs showed the presence of uniform sized (around 3 microns) particles. The BET surface area of the catalyst was 150 $m^2/g$. The lattice defects due to the incorporation of Yttrium in the $Zr^{4+}$ site of the zirconia lattice appears to enhance the number and strength of the Lewis acidity of the catalysts.

EXAMPLE 2

This example illustrates the procedure for the acceleration of the Diels-Alder reaction using yttrium based Lewis acid catalyst. A mixture of 0.198 g of cyclopentadiene and 0.158 g of 1,4 naphthoquinone and 0.075 g of the catalyst prepared according to the procedure given in the example 1 above, in 10 ml of dichloromethane was stirred at room temperature for 5 h. The catalyst was filtered off. After evaporation of solvent, the residue was chromatographed over silica gel column by eluting with 5% acetone/petroleum ether to give 0.2083 g of endo adduct, Endo tetracyco[$10.2.1.0_{2,11}.0^{4,9}$] pentadeca4,5,7,13-tetraene-3,10-dione.

EXAMPLE 3

In this example, D-A reaction of cyclopentadiene with 2-methyl-1,4-napthoquinone is described. The procedure involves refluxing of 0.66 g of cyclopentadiene, 0.158 g of 2-methyl-1,4-napthoquinone and 0.075 g of the sulfate modified yttria doped zirconia catalyst prepared according to the procedure described in the example 1, was refluxed in 10 ml of benzene at 90° C. for 10 h. The catalyst was filtered off. After evaporation of solvent, the residue was chromatographed over silica gel column by eluting with 5% acetone/petroleum ether to give 0.203 g of endo adduct, Endo-tetracyclo[$10.2.1.0.^{2,11}.0.^{4,9}$]pentadeca-2-methyl4,5,7,13-tetraene-3,10-dione (85% yield).

EXAMPLE 4

In this example, D-A reaction of cyclopentadiene with 7-isopropyl-10-methyloxaspiro(5,5)undec-3-ene-2,5-dione is described. The procedure involves stirring of a mixture of 0.132 g of cyclopentadiene, 0.158 g of 7-isopropyl-10-methyl-oxaspiro(5,5)undec-3-ene-2,5-dione and 0.05 g of sulfated zirconia catalyst doped with scandia prepared according to the procedure similar to that of example 1 above, was stirred in 10 ml of dichloromethane at room temperature for 8 h. The catalyst was filtered off. After evaporation of solvent, the residue was chromatographed over silica gel column by eluting with 5% acetone/petroleum ether to give 0.242 g of spiro{2'-isopropyl-5'methylcyclohexane-1,5,4,oxatricyclo[6.2.1.0.$^{2,7}$]undec-9-ene-3,6 dione} (85% yield).

EXAMPLE 5

In this example, D-A reaction of 1-methylbutadiene with 1,4-napthoquinone is described. The procedure involves stirring of 0.136 g 1-methylbutadiene, 0.158 g of 1,4-napthoquinone and 0.08 g of sulfated zirconia doped with lanthana catalyst prepared according to the procedure similar to that described in the example 1 above, in 10 ml of dichloromethane at room temperature for 20 h. The catalyst was filtered off. After evaporation of solvent, the residue was chromatographed over silica gel column by eluting with 5% acetone/petroleum ether to give 0.15 g of endo adduct, endo-tricyclo[4.4.2.0$^{2,7}$0$^{9,14}$]tetradeca-3-methyl]4,10,12,14-tetraene-1,8-dione. (65% yield).

EXAMPLE 6

In this example, D-A reaction of cyclohexadiene with 1,4-napthoquninone is described. The procedure involves stirring of 0.164 g of cyclohexadiene 0.158 g 1,4-napthoquinone and 0.075 g of sulfated zirconia catalyst doped with yttria prepared according to the procedure similar to that described in example 1 above, in 10 ml of dichloromethane at room temperature for 48 h. The catalyst was filtered off. After evaporation of solvent, the residue was chromatographed over silica gel column by eluting with 5% acetone/petroleum ether to give 0.107 g of endo adduct, endo-tetracyclo[10.2.1.0$^{2,11}$0$^{4,9}$]hexadeca-4,5,7,13-tetraene-3,10-dione.

EXAMPLE 7

In this example, D-A reaction of cyclopentadiene with 1,4-benzoquinone is described. 0.132 g of cyclopentadiene 0.108 g of 1,4-benzoquinone and 0.025 g of the sulfated zirconia catalyst doped with yttria prepared according to the procedure similar to that described in the example 1 above, was stirred in 10 ml of dichloromethane at room temperature for 8 h. The catalyst was filtered off. After evaporation of solvent, the residue was chromatographed over silica gel column by eluting with 5% acetone/petroleum ether to give 0.17 g of endo adduct, endo-tricyclo[6.2.1.0$^{2,7}$]undeca4,9-diene-3,6-dione. (92% yield).

EXAMPLE 8

In this example, D-A reaction of cyclopentadiene with cyclohexenone is described. The procedure involves refluxing of 0.66 g of cyclopentadiene, 0.096 g of cyclohexenone and 0.05 g of the catalyst sulfated zirconia doped with lanthana prepared according to the procedure described in the example I above, in 10 ml of toluene at 90° C. for 10 h. The catalyst was filtered off. After evaporation of solvent, the residue was chromatographed over silica gel column by eluting with 5% acetone/petroleum ether to give 0.107 g of endo adduct, endo-tricyclo[6.2.1.0$^{2,7}$]undeca-9en-3-one (66% yield).

EXAMPLE 9

In this example, D-A reaction of cyclopentadiene with ethyl acrylate is described. The procedure involves stirring of 0.132 g of cyclopentadiene, 0.110 g of ethyl acrylate and 0.055 g of the sulfated zirconia catalyst doped with yttria prepared according to the procedure described in example 1 above, in 10 ml of dichloromethane at room temperature for 5 h. The catalyst was filtered off. After evaporation of solvent, the residue was chromatographed over silica gel column by eluting with 5% acetone/petroleum ether to give 0.156 g of endo adduct, bicyclo[2.2.1.]2-carboethoxy-hept-5-ene. (94% yield).

EXAMPLE 10

In this example, inverse electron demand D-A reaction of acrolein with 3,4-tetrahydropyran is described. The procedure involves refluxing of 0.056 g of acrolein, 1.68 g of tetrahydropyran and 0.30 g of the catalyst prepared according to example 1 above in 10 ml of benzene at 60 (C 20 h. The catalyst was filtered off. After evaporation of solvent, the residue was chromatographed over silica gel column by eluting with 5% acetone/petroleum ether to give 0.12 g of endo adduct, 1,9-dioxabicyclo[4.4.0$^{5,10}$]dec-2-ene

EXAMPLE 11

In this example, ene reaction of citranelol to isopulegol is described. The procedure involves refluxing of 0.5 g citranelol in dry hexane and 0.05 g of the catalyst prepared according to the example 1 at 60° C. for 10 h. The catalyst was filtered off. After evaporation of solvent, the residue was chromatographed over silica gel column by eluting with 5% acetone/petroleum ether to give 0.325 g of isopulegol (65% yield).

Advantages of the present invention:

The process of the present invention shows a significant improvement over prior art processes of the Diels-Alders reaction. The endo selectivity and the yield of the product is high under very simple operational conditions.

Another advantageous feature of the process of the present invention is that reaction is carried out at room temperature unlike the several C—C bond forming reactions which are known to take place at reflux temperature.

Yet another advantageous feature of the process of the present invention is the use of solid acid catalysts which are absolutely non-hazardous unlike the Lewis acids such as Triflic acid or hydrofluoric acid or complexes such as Yttrium triflates or scandium trifaltes.

The most significant advantageous feature of the present invention is that the most difficult and less reactive dienopile undergo D-A reaction with a variety of diene to give excellent yield of the product.

We claim:

1. A process for the preparation of organic compounds through C—C bond forming reaction which comprises reacting a diene with dienophile in a solvent and in the presence of a solid acid catalyst based on either yttrium or scandium or lanthanum supported on a metal oxide support comprising oxides of zirconium or tin or titanium or iron modified by sulphation for a period ranging from 5 to 48 hours and recovering reaction products from the reaction mixture by filtration and removal of the solvent by evaporation followed by column chromatography.

2. A process as claimed in claim 1 wherein, the catalyst is a heterogenous catalyst.

3. A process as claimed in claim 1 wherein the C—C bond forming reaction is selected from the group consisting of a Diels-Alder reaction, a Hetero-Diels-Alder reaction, an inverse electron demand Diels-Alder reaction, and an ene reaction.

4. A process as claimed in claim 1 wherein, the molar content of yttria or scandia or lanthana in the solid acid catalyst ranges from 1 mole % to 40 mole %.

5. A process as claimed in claim 1 wherein the dienophile is selected from the group consisting of 1,4-napthoquinone, Juglone, 2-methyl-1,4-napthoquinone, maleic anhydride, benzoquinone, cyclohexanone, acrylic acid, ethyl or methyl acrylate, 3,4-dihydro-2H-pyran, spiro(4.4)non-2,3-ene-1,4-dione, methacrolein, nitroso compounds, 7-isopropyl-10-methyl-1-oxaspiro(5.5)undec-3-ene-2,5-dione, methyl vinyl ketone, imines, N-sulfuryl sulfonamides, N-ethylmaleimide, 10-phenyl-1-oxaspiro(5,5)cyclohexyl-3-ene-2,4-dione, 2,5-dihydrothiophene-3,4-dicarboxylic anhydride, Dialkyl, diaryl or aryl-alkyl maleates and fumarates, alkyl or aryl glyoxalates, alkyl or aryl pyruvates, vinyl ethers, cis-butenediol derivatives and cyclic sulfites and ketals.

6. A process as claimed in claim 1 comprising mixing the diene and the dienophile in the solvent with stirring at room temperature in the presence of the solid acid catalyst.

7. A process as claimed in claim 1 wherein the C—C bond forming reaction is a Diels-Alder reaction that is selected to give excellent yield of endo product with high selectivity.

8. A process as cliamed in claims 1 to 7 wherein, the solid acid catalyst is environmentally friendly, easily recoverable from the reaction mixture and recyclable.

9. A process as claimed in claim 1 comprising mixing the diene and dienophile in the solvent and heating to a temperature between 40 and 80° C. with stirring in the presence of the solid acid catalyst.

10. A process as claimed in claim 1 wherein the diene is selected from the group consisting of cyclopentadiene, 1,3-cyclohexadiene, 1-meth,1-1,3-butadiene, 2-trimethylsilyloxy-1,3-butadiene, 1-methoxy-3-trimethylsilyloxy-1,3-butadiene, acrolein, furan, benzoisofuran, 1-methoxy-1,3-cyclohexadiene, hexachlorocyclopentadiene, 2,3-dimethylbutadiene, 4-methoxyisoxazole and unsaturated hydrazone.

* * * * *